United States Patent
Clay

(10) Patent No.: US 10,247,740 B2
(45) Date of Patent: *Apr. 2, 2019

(54) DETECTOR ARRANGEMENT FOR BLOOD CULTURE BOTTLES WITH COLORIMETRIC SENSORS

(71) Applicant: bioMerieux, Inc., Durham, NC (US)

(72) Inventor: Bradford G. Clay, Wildwood, MO (US)

(73) Assignee: bioMerieux, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/240,011

(22) Filed: Aug. 18, 2016

(65) Prior Publication Data

US 2016/0356797 A1    Dec. 8, 2016

Related U.S. Application Data

(63) Continuation of application No. 13/352,428, filed on Jan. 18, 2012, now Pat. No. 9,447,372, which is a continuation-in-part of application No. 13/185,898, filed on Jul. 19, 2011, now Pat. No. 9,739,788.

(60) Provisional application No. 61/400,001, filed on Jul. 20, 2010.

(51) Int. Cl.
*G01N 33/84* (2006.01)
*G01N 21/78* (2006.01)
*G01N 21/80* (2006.01)
*C12M 1/34* (2006.01)
*G01N 21/31* (2006.01)

(52) U.S. Cl.
CPC ............ *G01N 33/84* (2013.01); *C12M 41/26* (2013.01); *C12M 41/34* (2013.01); *C12M 41/36* (2013.01); *G01N 21/3151* (2013.01); *G01N 21/78* (2013.01); *G01N 21/783* (2013.01); *G01N 21/80* (2013.01); *G01N 2021/3181* (2013.01); *G01N 2201/127* (2013.01)

(58) Field of Classification Search
None
See application file for complete search history.

(56) References Cited

U.S. PATENT DOCUMENTS

| 4,945,060 A * | 7/1990 | Turner | C12M 41/26 |
| | | | 435/288.7 |
| 5,013,155 A * | 5/1991 | Rybak | G01N 21/03 |
| | | | 250/228 |
| 5,952,218 A * | 9/1999 | Lee | C12M 23/08 |
| | | | 211/74 |

* cited by examiner

*Primary Examiner* — Xiaoyun R Xu

(57) ABSTRACT

A detector arrangement is disclosed for a blood culture bottle incorporating a colorimetric sensor which is subject to change of color due to change in pH or $CO_2$ of a sample medium within the blood culture bottle. The detector arrangement includes a sensor LED illuminating the colorimetric sensor, a reference LED illuminating the colorimetric sensor, a control circuit for selectively and alternately activating the sensor LED and the reference LED, and a photodetector. The photodetector measures reflectance from the colorimetric sensor during the selective and alternating illumination of the colorimetric sensor with the sensor LED and the reference LED and generates intensity signals. The reference LED is selected to have a peak wavelength of illumination such that the intensity signals of the photodetector from illumination by the reference LED are not substantially affected by changes in the color of the colorimetric sensor.

12 Claims, 7 Drawing Sheets

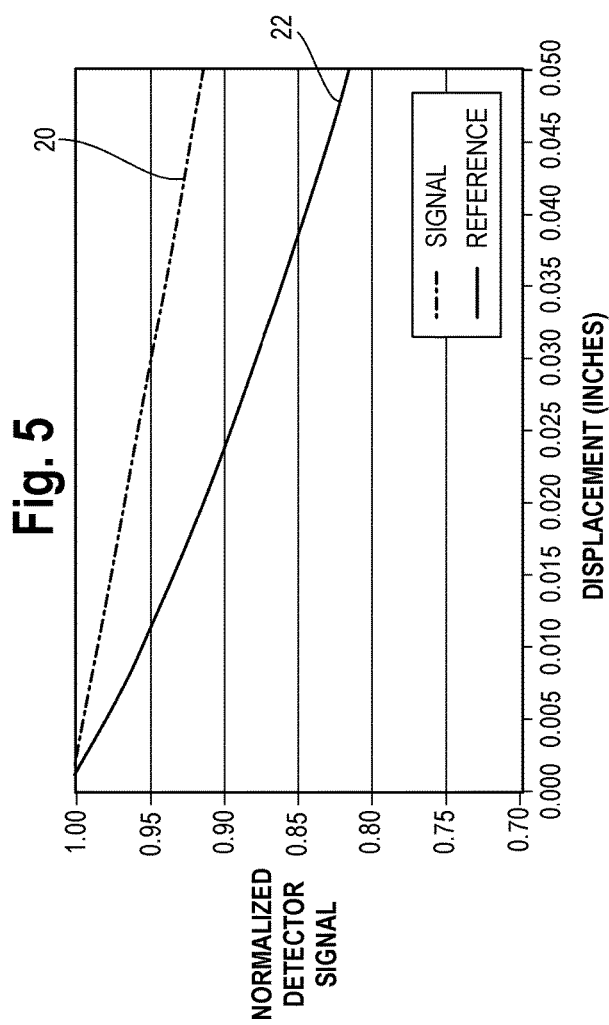
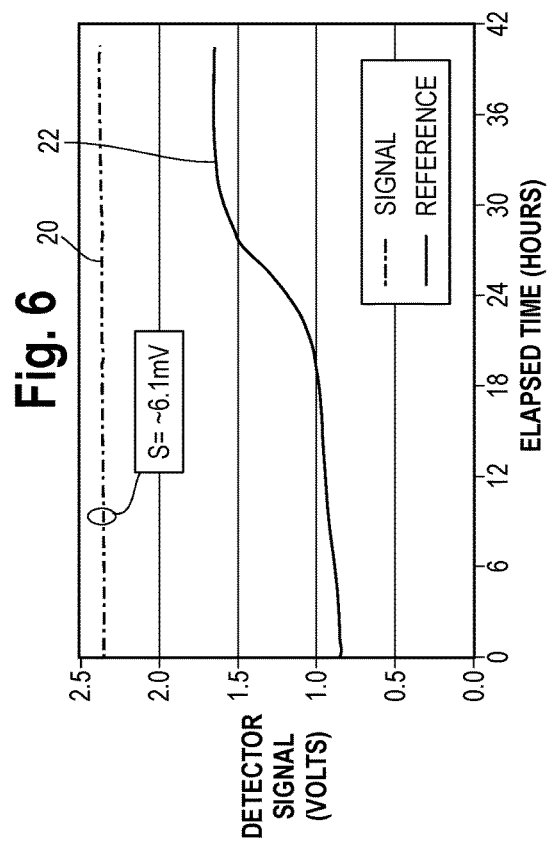

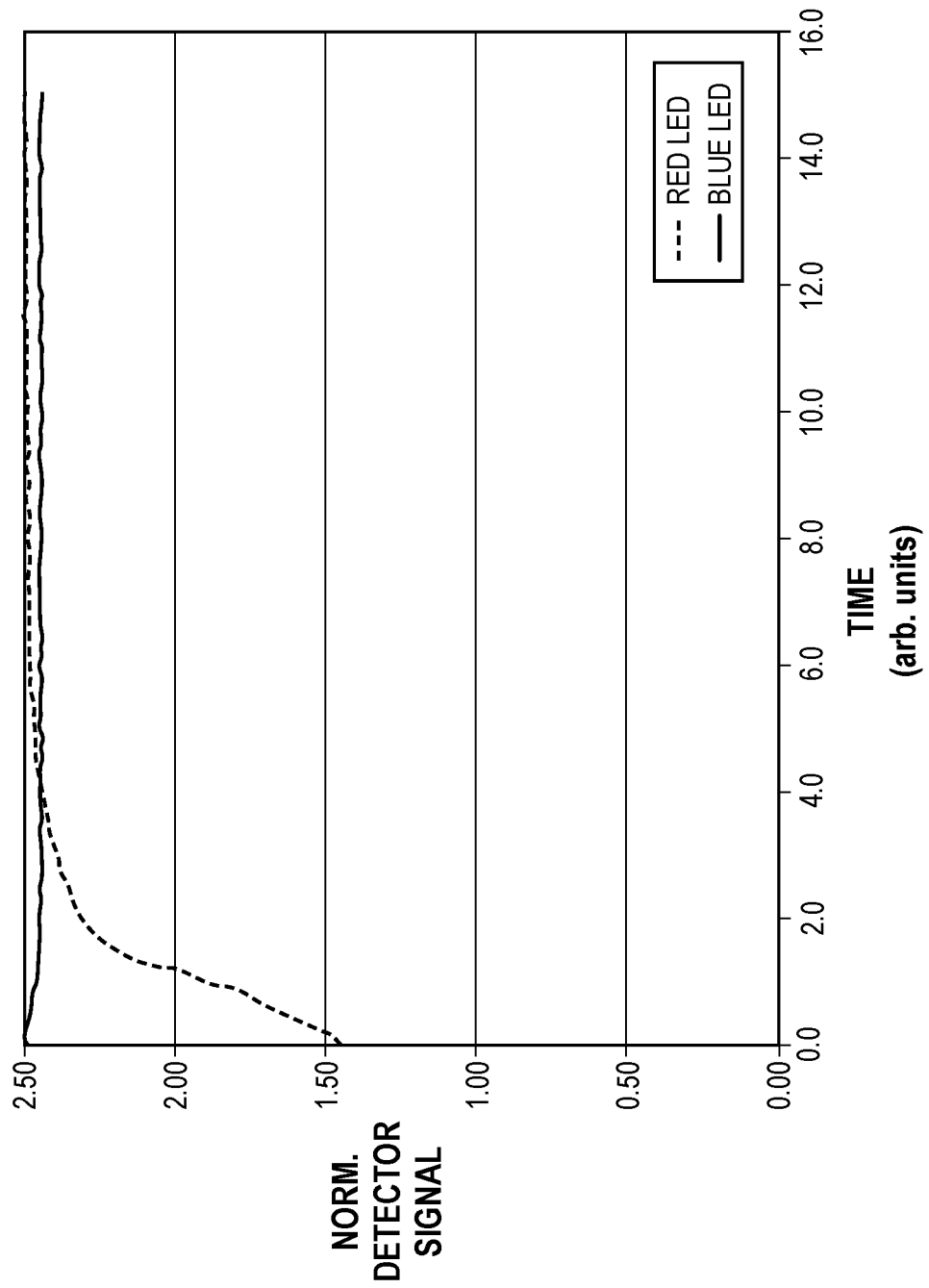

DETECTOR ARRANGEMENT FOR BLOOD CULTURE BOTTLES WITH COLORIMETRIC SENSORS

CROSS REFERENCE TO RELATED APPLICATION

This application is a continuation of U.S. patent application Ser. No. 13/352,428, entitled "Detector arrangement for blood culture bottles with colorimetric sensors, filed Jan. 18, 2012, which is a continuation-in-part of U.S. patent application Ser. No. 13/185,898 filed Jul. 19, 2011, which claims priority benefits under 35 U.S.C. § 119 (e) to U.S. Provisional Patent Application No. 61/400,001 filed Jul. 20, 2010, which is incorporated herein.

BACKGROUND

Bottles for culturing of blood for the presence of microorganism and related instruments for analyzing such bottles in a noninvasive manner are known in the art and described in the patent literature. See U.S. Pat. Nos. 5,858,769; 5,795,773; 4,945,060; 5,094,955; 5,164,796; 5,217,876; and 5,856,175. The bottles and instruments of the above-listed patents have been commercialized with success by the present assignee under the trademark BacT/ALERT.

The bottles described in these blood culture instruments utilize colorimetric sensors placed in the bottom of the bottle and in contact with the sample media to determine the presence/absence of bacterial growth. Once a clinical/industry sample is added to the liquid growth media present in the bottle and incubation occurs, the concentration of carbon dioxide increases as the number of microorganisms increase; carbon dioxide is a respiration by-product of bacterial growth. Alternatively, changes to the media pH that are related to the growth of microorganisms can also be monitored by the sensor. The basic operation of the BacT/ALERT sensor and monitoring electronics is described in U.S. Pat. No. 4,945,060 and also in an article by Thorpe et. al. in "BacT/Alert: an Automated Colorimetric Microbial Detection System" which was published in the Journal of Clinical Microbiology, July 1990, pp. 1608-12. The '060 patent and the Thorpe et al. article are incorporated by reference here.

The basic colorimetric sensing system described in the '060 patent is shown in FIG. 1 of the appended figures. A red Light Emitting Diode (LED) (4) shines onto the bottom of the BacT bottle (1). A colorimetric sensor (2) is deposited onto the bottom of the bottle (1). The LED light impinges on the sensor at a 45 degree angle relative to the bottom surface of the bottle (1). The majority of the light penetrates the structure of the bottle and impinges on the colorimetric sensor (2). Part of the light will reflect off the plastic bottle material and sensor (2) at 45 degrees to the bottom surface of the bottle, but in an opposite direction to the impinging light (e.g. the angle of reflection is equivalent to the angle of incidence). Much of the remaining light is scattered from the surface and interior of the sensor. The sensor (2) changes its color as the percentage of $CO_2$ in the bottle varies from 0% to 100%; the color varies from blue to yellow, respectively. A silicon photodetector (5) "stares" (i.e., continuously monitors the scattered intensity signal) at the region in the sensor (2) where the light from the LED interacts with the sensor. The intensity of the scattered light that is detected by the photodetector is proportional to the $CO_2$ level within the bottle (1). FIG. 1 also shows the associated electronics including a current source (6), current-to-voltage converter (7) and low pass filter (8).

FIG. 2 is a plot of the signal received by the photodetector (5) of FIG. 1. The data was collected using a fiber optic probe in place of the photodetector (5) in FIG. 1. The fiber optic probe is routed to a visible light spectrometer, which shows the scattered light as a function of intensity (Reflectance Units) and wavelength. The shape of each curve is the convolution of the LED intensity distribution with the reflectivity of the colorimetric sensor (2) at a specified $CO_2$ level.

When the silicon photodetector (5) of FIG. 1 is substituted for the fiber optic probe, a photocurrent is generated by the photodetector that is proportional to the integrated wavelength signal shown in FIG. 2. In other words, the silicon photodetector (5) integrates the spectral response into a photocurrent. In turn, this photocurrent is converted into a voltage signal using a transimpedance amplifier.

While the BacT/ALERT sensing system of FIG. 1 is robust and has been used in blood culture systems successfully for many years, it does have a few areas for improvement. First, if the blood culture bottle (1) moves in the cell (e.g. displacement in the z-axis so that it shifts away from the position of the photodetector), the system (as it is currently implemented) detects this movement as a reduction in intensity. However, this reduction in intensity is interpreted by the instrument as reduction in $CO_2$ level in the bottle, which may not in fact be occurring. Since this effect is counter to the effect of a bottle's reflectivity increasing as carbon dioxide content increases (signifying bacterial growth), it is possible that the system would treat a translating bottle as having no growth (i.e., a false negative condition).

Likewise, as the instrument ages in the clinical laboratory, the optical system may collect dust or optical materials experience reduced transmissivity as a function of time. For example, as plastics age, their transmissivity can be reduced by the effects of light, particulate buildup (dust) or repeated use of cleaning agents. These effects would not affect readings but would manifest as a drift in the response of the system. Periodic calibration checks could compensate for this drift. Thus, there is a long-felt but unmet need to have a real-time monitor of the transmission in the optical system and the capability to adjust or compensate for some of these sources of error, particularly the situation where the bottle is not fully installed in the receptacle and is not at the nominal or home position (has some Z-axis displacement away from the optical detector arrangement).

Other prior art of interest includes the following U.S. Pat. Nos. 7,193,717; 5,482,842; 5,480,804; 5,064,282; 5,013,155; 6,096,272; 6,665,061; 4,248,536 and published PCT application WO 94/26874 published Nov. 24, 1994.

SUMMARY

An improved detection arrangement for blood culture bottle incorporating colorimetric sensors is disclosed.

The detection arrangement includes photodetector, a sensor LED and a reference LED, and a control circuit for selectively and alternately activating the sensor LED and the reference LED to illuminate the colorimetric sensor. The sensor LED functions like the LED of FIG. 1 and is used to determine the change in the colorimetric sensor color. The photodetector monitors the reflectance from the sensor when illuminated by the sensor LED by monitoring intensity changes. The reference LED is selected to have a wavelength such that the intensity readings of the photodetector from illumination by the reference LED are not substantially affected by changes in the color of the colorimetric sensor.

As such, the reference LED can be used as a reference, with the photodetector readings during illumination by the reference LED substantially unaffected by changes in $CO_2$ concentration within the bottle. It has been found that wavelengths in the near infra-red (peak λ for the LED between 750 and 950 nm) are suitable for the reference LED. It has also been found that wavelengths in the blue portion of the spectrum are also suitable for the reference LED, with the LED having a peak λ of below about 490 nm, as will be explained in greater below. Reference LED's in the blue portion of the spectrum may produce minor changes in the reading the colorimetric sensor, and in particular it may cause the reflected signal from the colorimetric sensor under illumination from the sensor LED to drop slightly under conditions of low $CO_2$ concentrations within the bottle. However, there are other benefits that blue reference LEDs offer as will be explained below. The small effect of the blue reference LED on the reflected signal from the sensor LED is sufficiently minor that, in the overall sense, the reference LED does not substantially affect the detection of the changes of the color of the colorimetric sensor in the bottle due to conditions of microbial growth in the bottle.

The reference LED is useful to indicate if the distance between the bottle and the detector subassembly changes, ambient lighting conditions change, or anything within the physical optical path between the sensor LED, the bottle and the photodetector changes. Since a change in the reference LED is not dependent on the state of the colorimetric sensor, the reference LED can provide information about changes in the optical system that are not related to microorganism growth so that such non-growth related changes from the system can be discriminated from growth-related changes. This feature helps reduce the false-positive rate in the system and improves sensing accuracy and reliability.

In use, the sensor LED and reference LED are illuminated alternately and repeatedly, e.g., in a time division multiplexed manner. The photodetector signals from such sequential illuminations are fed to a computer. The computer monitors changes in the photodetector signal when the reference LED illuminated; these changes would indicate a change in the bottle position or the optical system. The computer can compensate the sensor LED signals according to derived calibration relationships between the sensor LED and reference LED signals, e.g., due to offset of the bottle position in the detection system from a home or nominal position.

BRIEF DESCRIPTION OF THE DRAWINGS

FIG. 5 is a graph of photodetector intensity signals for the sensor LED and reference LED as a function of bottle displacement from nominal or home position in which the bottle is in its designed position proximate to the detection system of FIG. 3.

FIG. 6 is a plot of photodetector intensity signals for the sensor LED and reference LED as a function of time during conditions of microbial growth with the bottle.

FIG. 12 is a plot of the signal of the photodetector of FIG. 3 as a function of time under normal conditions of bacterial growth within the bottle.

DETAILED DESCRIPTION

Figure 3:
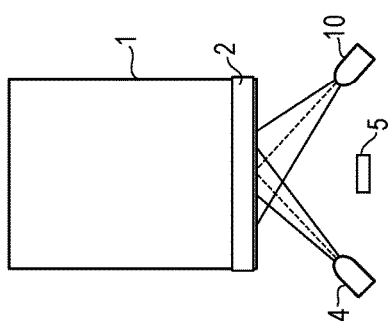
FIG. 3 is a sensor and detector arrangement for blood collection bottles in accordance with the present disclosure.

The invention involves the use of secondary LED as a light source to compensate for non-Liquid Emulsion Sensor (LES) changes to the optical system. A block diagram of the optical configuration is shown in FIG. 3. The configuration is for testing a bottle 1 having a colorimetric LES (sensor) 2 incorporated within the bottle 1. The configuration includes a sensor LED 4, a reference LED 10, and a photodetector 5 generating intensity signals. Both LEDs 4 and 10 are angled at 45 degrees in relation to the bottom surface of the bottle as shown in FIG. 3. The reflectivity of the bottle bottom and LES 2 is measured sequentially, by means of a control circuit (42, FIG. 7) which selectively and alternately activates the sensor LED and the reference LED. For example, the sensing or red LED 4 is turned on and the reflected signal is measured by the photodetector 5. The sensing LED 4 is then extinguished. The reference LED 10 is then illuminated and the same photodetector 5 measures the reflected light. Then it is extinguished, and the process is repeated. This approach is also referred to as a time-division multiplexed scheme, which is shown in FIG. 8 and will be described in further detail below.

As noted above, the LEDs 4 and 10 are oriented at a 45 degree angle relative to the bottom of the bottle. This is so that the reflection off of the bottom surface of the bottle is not strongly coupled into the photodetector 5. The angle of incidence=angle of reflection so that light striking the bottle bottom will exit off at 45 degrees and will not strongly affect the photodetector reading (since scattered light from the LES is only of interest). The LEDs have a spatial emission angle of 15-17 degrees; i.e., the LEDs emit light in a cone that is defined by Peak Emission and Full-Width angle at half maximum power; the angle of the cone is in the range of 15-24 degrees.

Testing was performed on a variety of LED colors, and it was found that the signal of the photodetector for near-infrared LEDs (peak wavelength from 750-950 nm) were marginally effected by the LES color changes. All other wavelengths of light had a negative or positive change in reflectivity as the CO2 level was changed from 0% to 100%. This effect minimizes at wavelengths beyond about 750 nm (near-infrared LED) as is shown in Table 1.

TABLE 1

Photodetector output (volts) with CO2 spiked bottles
For sensing (RED) LED and reference (IR) LED

| $CO_2$ Level | Samples | Sensing LED Mean | Std. Dev. | Reference LED Mean | Std. Dev. |
|---|---|---|---|---|---|
| 0% | 390 | 0.65838 | 0.00045 | 2.32539 | 0.00045 |
| 2% | 390 | 0.84627 | 0.00048 | 2.25763 | 0.00048 |
| 15% | 390 | 1.29105 | 0.00047 | 2.40419 | 0.00048 |
| 100% | 390 | 1.92822 | 0.00063 | 2.29345 | 0.00050 |

Figure 4:
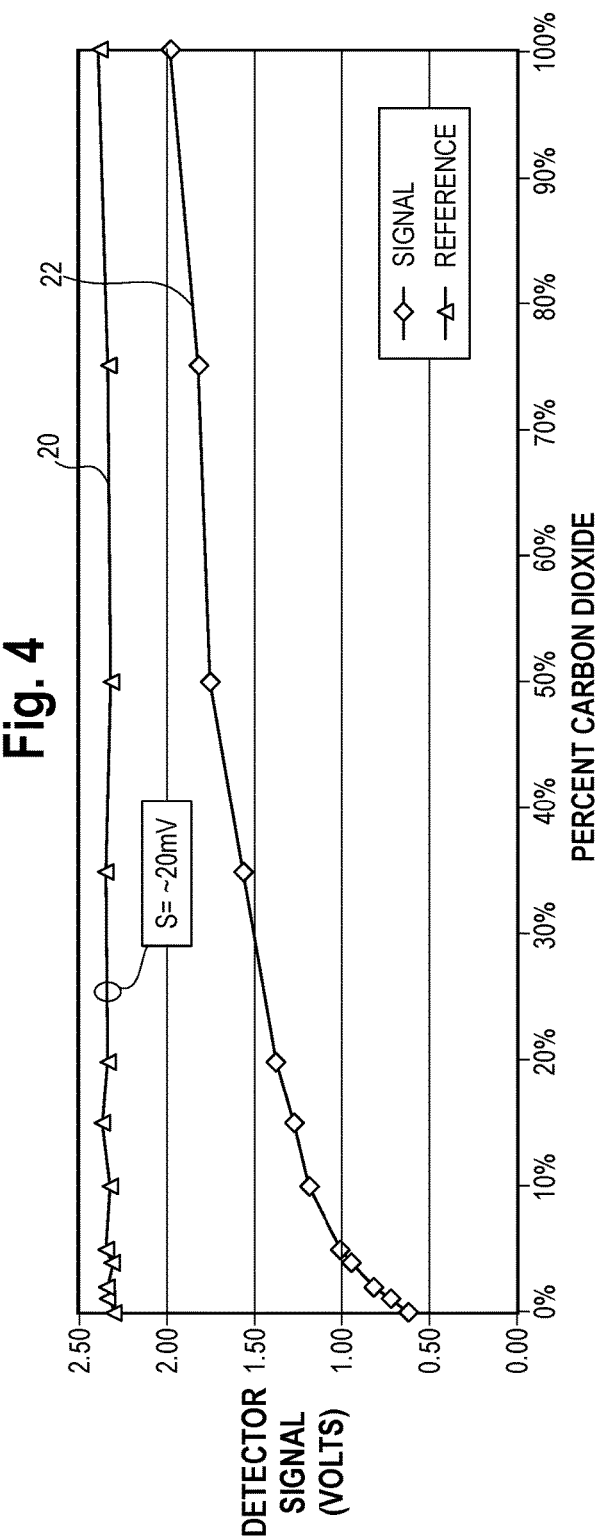
FIG. 4 is a plot of intensity signals from the photodetector of FIG. 3 for sensor LED and reference LED illumination of the colorimetric sensor over 0-100% $CO_2$ range present within the bottle.

FIG. 4 shows the graphical equivalent of Table 1. The photodetector readings for the reference sensor are plotted as line 20 and the photodetector readings for the sensor LED are plotted as line 22. A large increase in the red LED signal 22 is seen in the graph (it changes from about 0.6 volt to almost 2 volts) as the carbon dioxide level in the bottle is increased from 0% $CO_2$ to 100% $CO_2$. At the same time, the Reference LED signal 20 changes from 2.32 volts to 2.29 volts (a change of 30 mV), so it is very stable over the course of the LES changing color.

In order to study the changes in the optical signal as a function of the bottle position in relation to the optical system, a calibration/test fixture was constructed consisting of a digital micrometer that is attached to the BacT/ALERT bottle. The bottle is first placed in the normal (home) position in the BacT/ALERT rack assembly so that it is as close to the optical system as is possible. Readings of the reflectance are taken, then the bottle is displaced by adjusting the micrometer. The micrometer provides precise small adjustments to the z-axis displacement (i.e. it moves the bottle further from the optical system) so that the effects of displacement can be quantified. The normalized change in optical signal as a function of the displacement is shown graphically in FIG. 5, again with photodetector signal for illumination of the reference LED plotted as line 20 and the photodetector signal for the sensor LED plotted as line 22. It is seen that the displacement causes a linear shift in the signals received by the photodetector. While the sensor LED signal 22 and the reference LED signal 20 have different slopes of change, each is linear, so that a relationship can be developed to compensate for changes in the signal LED as a function of changes in the reference LED detector output, e.g., due to displacement of the bottle from a home or nominal position. Equations were computed for the graphs in FIG. 5; the equations are listed below in table 2 along with the goodness of fit parameter (R2).

TABLE 2

| Detector_output (Signal) = 0.2652 − 0.2554x | R2 = 0.9963 |
| Detector_output(Reference) = 0.5621 − 0.2384x | R2 = 0.9999 |

Where x = the linear displacement distance (in inches)

Accordingly, by mapping the change in intensity of the reference LED's output, a displacement value can be determined. Applying that value to the signal LED's output, the amount of intensity reduction can be quantified and compensated for.

A further test of the capabilities of the detector arrangement of FIG. 3 was performed by injecting a inoculum of Saccharomyces cerevisiae into the blood culture bottle and monitoring the colorimetric sensor using the sensor LED and reference LED optics while the yeast grows in the bottle. FIG. 6 shows the growth curve of the yeast growth—lag, exponential and stationary growth phases are shown. During the growth (and changes in the response of the LES sensor), it is seen that the reference LED signal 20 is unchanging, whereas the sensor LED signal 22 changes due to change in $CO_2$ concentration as a result of microbial growth. The flatness of the curve 20 verifies the insensitivity of the photodetector readings during illumination of the reference LED to changes in the LES color. It further verifies its ability to monitor changes in the optical system while not being affected by bacterial growth.

Figure 7:
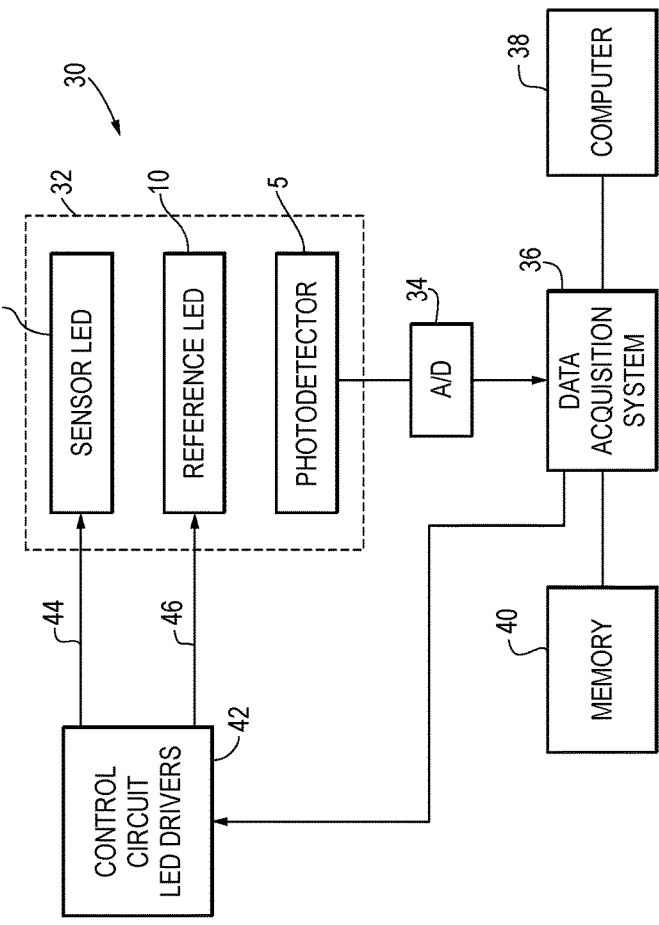
FIG. 7 is a block diagram of the electronics operating the sensor arrangement of FIG. 3.
Figure 8:
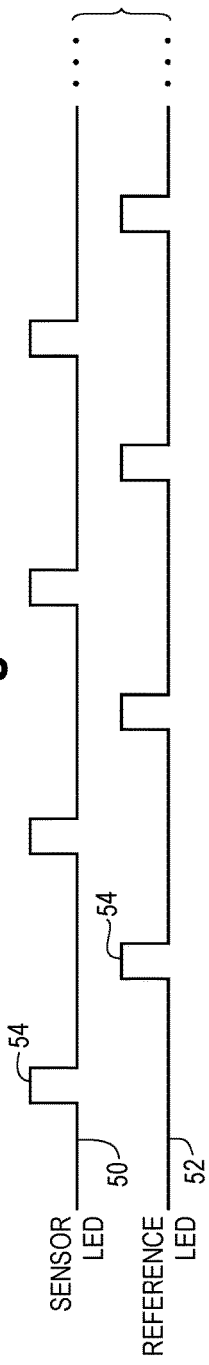
FIG. 8 is a graph of the duty cycle of the reference and sensor LED of FIG. 3, showing the time division multiplexing method of operation. The width of the pulses representing the duty cycle is not to scale; in one possible embodiment the duty factor is 33 percent: ⅓ of the time the reference LED is illuminated, ⅓ of the time the sensor LED is illuminated, and ⅓ of the time neither LED is illuminated to enable a "dark" measurement to be made.

FIG. 7 is a block diagram of the electronics 30 for the embodiment of FIG. 3. The electronics 30 includes an "optical nest" 32 consisting of the sensor LED 4, the reference LED 10, and the photodetector 5. The output of the photodetector is converted into a digital signal in an A/D converter 34 and fed to a data acquisition system 36. The data acquisition system sends signals to an LED control board 42 which includes control circuits and LED drivers which send signals over the conductors 44 and 46 to cause the LEDs 4 and 10 to illuminate in a time division multiplexed manner. Photodetector signals from the data acquisition system are sent to a computer 38, which may be part of the instrument incorporating the optical nest 32 of FIG. 7. (Incidental electronics such as filters and current-to-voltage converter are omitted in the Figure but may be present in the electronics).

Memory 40 stores the calibration constants and relationships between the reference and signal LED outputs, derived from curves such as FIG. 5 and explained above in Table 2. For example, the memory 40 stores a calibration relationship between intensity signals for the sensor LED as a function of distance of the bottle from the home position (plot 22 in FIG. 5); the computer 38 compensates for a drop in intensity signals from the sensor LED due to the bottle being positioned a distance away from the home position in accordance with calibration relationships for the sensor LED and the reference LED.

FIG. 8 is a graph of the duty cycle of the reference LED 10 and sensor LED 4 of FIG. 3, showing the time division multiplexing method of operation. The sensor LED on and off states are shown on line 50; the reference LED on and off states are shown in line 42. The width of the pulses representing the duty cycle is not to scale and can vary. In one possible embodiment the duty factor is 33 percent: ⅓ of the time the reference LED is illuminated, ⅓ of the time the sensor LED is illuminated, and ⅓ of the time neither LED is illuminated to enable a "dark" measurement to be made.

Compensation for dust, drift, changes in the optical system, and aging of the optical materials in the beam path are also possible with the arrangement of FIG. 3. Since these occur over an extended time (expected to be in the duration of months), they would be very slow changing. Compensation is achieved by saving data points from the initial calibration (e.g., derived from FIG. 5) and compare the photodetector signals for the IR LED 10 emission levels to initial values to compensate for degradation mechanisms in the optical system. This change would also be applied to the sensor LED 4. For shorter time period drift events, changes are monitored in the IR LED 10 which should be very steady over the growth cycle of bacteria; any changes in the IR LED performance cause adjustments in the sensor LED photodetector readings accordingly, e.g., using stored calibration relationships.

Blue Spectrum Reference LEDs

As noted above, it has also been found that the reference LED 10 (FIG. 3) with a peak wavelength of illumination below about 490 nm is also suitable for the present detector arrangements. In one embodiment, the reference LED has a peak wavelength of illumination of between about 328 and 470 nm. In a currently preferred embodiment, the reference LED has a peak wavelength of illumination of between about 450 and 470 nm. The Optek Technology OVLFB3C7 blue LED with a peak wavelength of 460 nm, a Lorentzian distribution of illumination intensity, and a spectral width of about 25 nm (435 to 485 nm total) is one example of a suitable reference LED.

Figure 1:
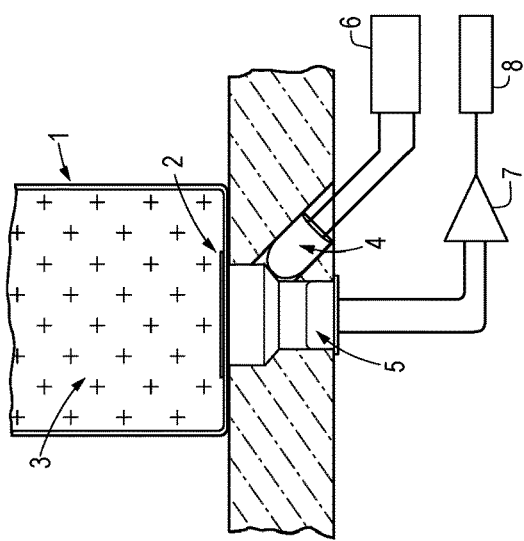
FIG. 1 is an illustration of a known sensor and detector arrangement for blood collection bottles as described in U.S. Pat. No. 4,945,060.
Figure 2:
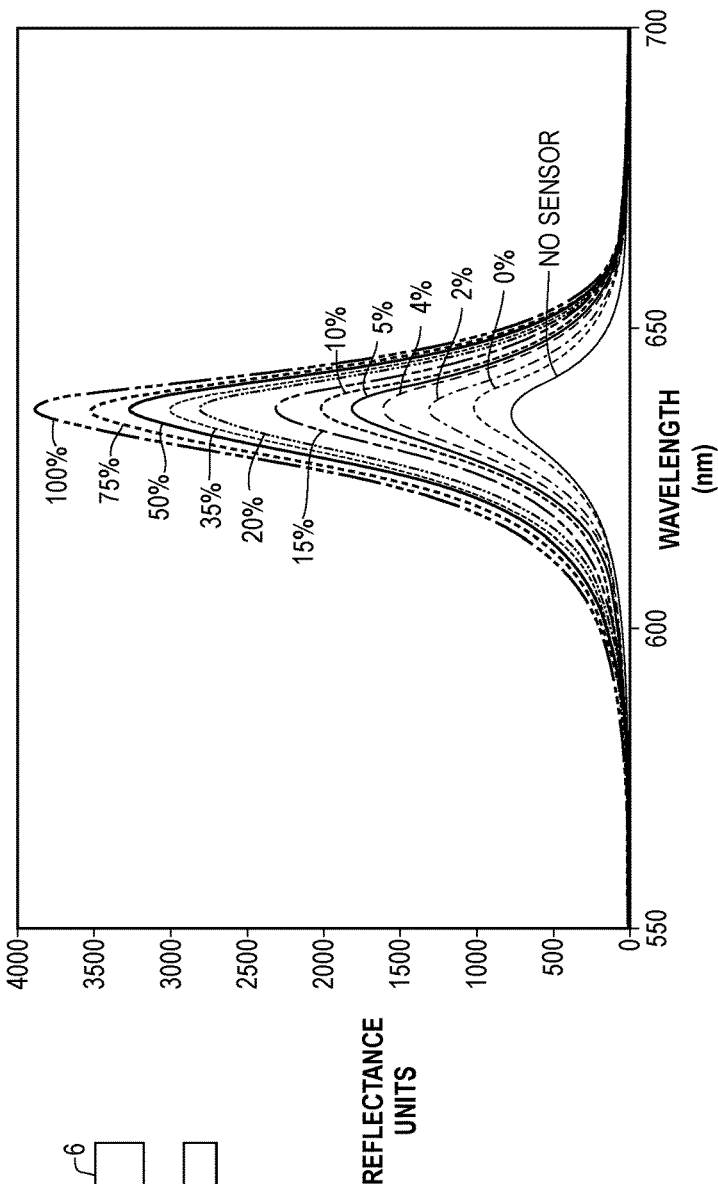
FIG. 2 is plot of reflectance of a colorimetric sensor on a spectrometer in place of the photodetector of FIG. 1 as a function of wavelength and $CO_2$ concentration.

This particular reference LED produces a minor change in readings from the colorimetric sensor (2, FIG. 3) as the sensor 2 changes color from blue to yellow under conditions of increasing microbial growth and concentration of $CO_2$ within the bottle. With the blue reference LED 10, the reflected signal from the sensor 2 drops slightly in the low values of $CO_2$ (predominantly between 0 to 5%). While the small change is signal is not ideal for a reference, the fact it drops rather than increases provides useful information. In particular, if the photodetector (5, FIGS. 1, 3) signals during illumination from the reference and sensor LEDS are both going in the same direction it is indicative of an error condition. Increasing photodetector signal during illumination from the sensor LED while the signal from the blue (reference) LED decreases or is unchanging is the normal state. See FIG. 12. A condition of photodetector signal decreasing under sensor LED illumination while photodetector signal increasing under blue (reference) LED illumination should never occur, unless the system is operating erratically.

Figure 9:
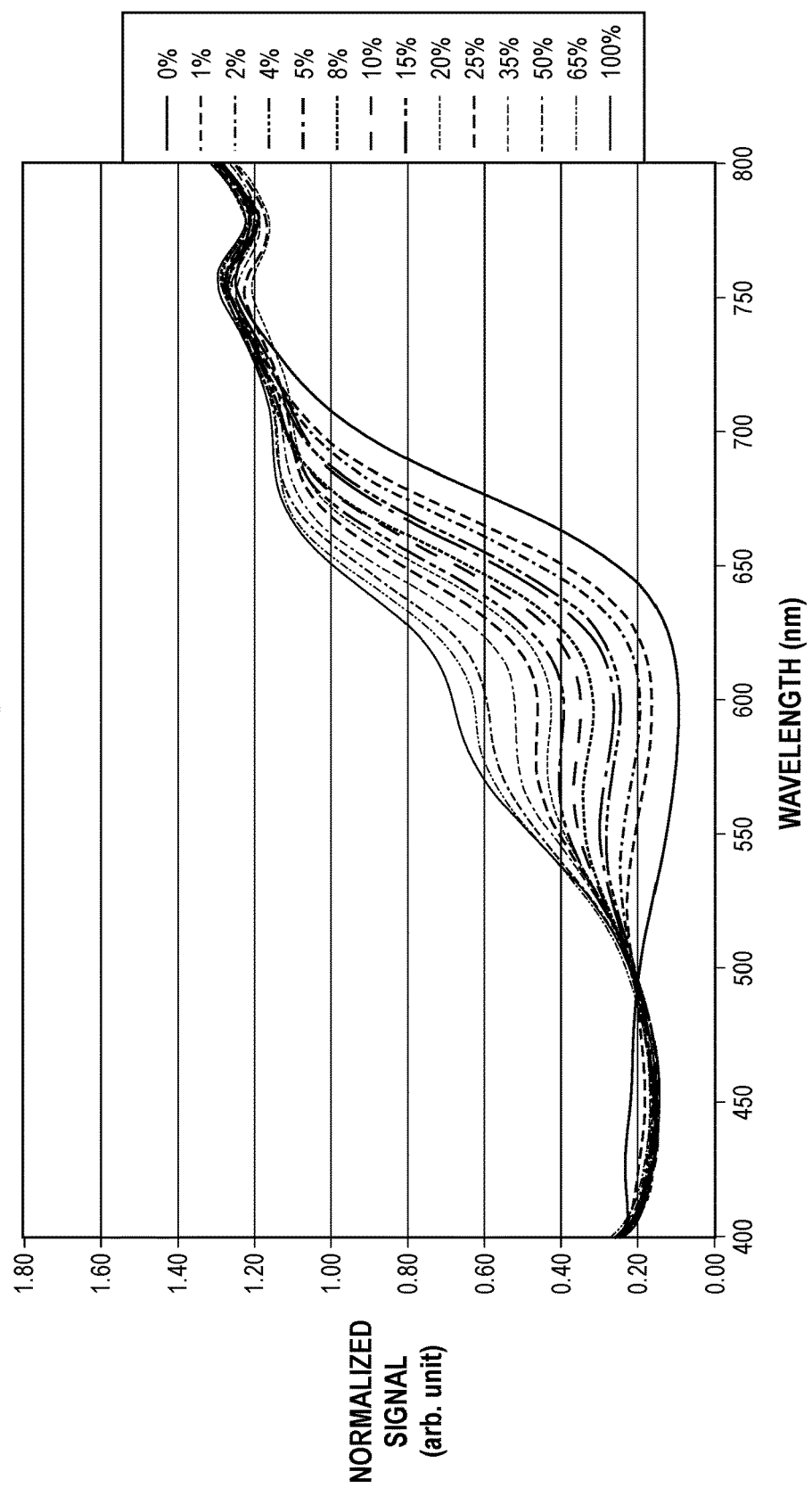
FIG. 9 is a plot of the spectral characteristics of a colorimetric sensor of FIG. 3 as a function of incident radiation under conditions of different concentrations of $CO_2$ within the bottle.

The blue wavelength of the reference LED also has some characteristics with its interaction with the colorimetric sensor 2 (FIGS. 1, 3) that may provide additional data. FIG. 9 shows the spectral characteristics of the sensor 2 as a function of incident wavelength on a line in the graph. The series of lines correspond to the spectral response of the sensor as a function of $CO_2$ level in the BacT bottle 1 (i.e. each line is the spectrum at one discrete $CO_2$ level). The sensing LED (4, FIG. 3) operates in the 635-640 nm or red region of the optical spectrum; it can be noted that this corresponds to a region of large change in signal as $CO_2$ level changes.

Figure 10:
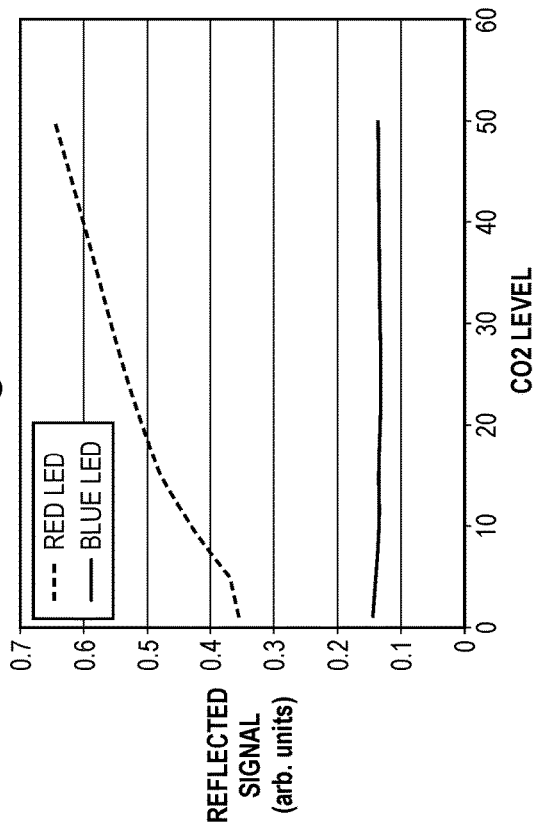
FIG. 10 is a plot of the signal of the photodetector of FIG. 3 as a function of $CO_2$ concentration within the bottle under illumination by a sensor LED (red line) and a blue spectrum reference LED (blue line).

Note that in FIG. 9, the signal change under different CO2 concentrations in the blue region (below about 490 nm) is much smaller than the signal change at 635 nm, indicating that a blue reference LED does not result in a substantial effect on the output of the colorimetric sensor as $CO_2$ concentration changes. FIG. 10 shows the changes in the photodetector signals for two LEDs (reference or blue LED and the sensor or "red" LED) as a function of $CO_2$ in the BacT/ALERT bottles. Note that the photodetector signal under conditions of illumination by the blue (reference) LED signal actually drops slightly as $CO_2$ concentration increases in the bottle, whereas the photodetector signal increases substantially under conditions of illumination by the sensor LED as $CO_2$ concentration increases in the bottle. This opposite slope information can be used to help discriminate changes in the colorimetric sensor versus changes in the system. In a normal operating condition, the photodetector signal for red or sensor LED illumination will increase if there is bacterial growth in the bottle ($CO_2$ level in the bottle will increase). The photodetector signal for the blue (reference) LED signal will decrease slightly. This information will indicate a normal state for the bottle. This is shown in FIG. 12.

Figure 11:
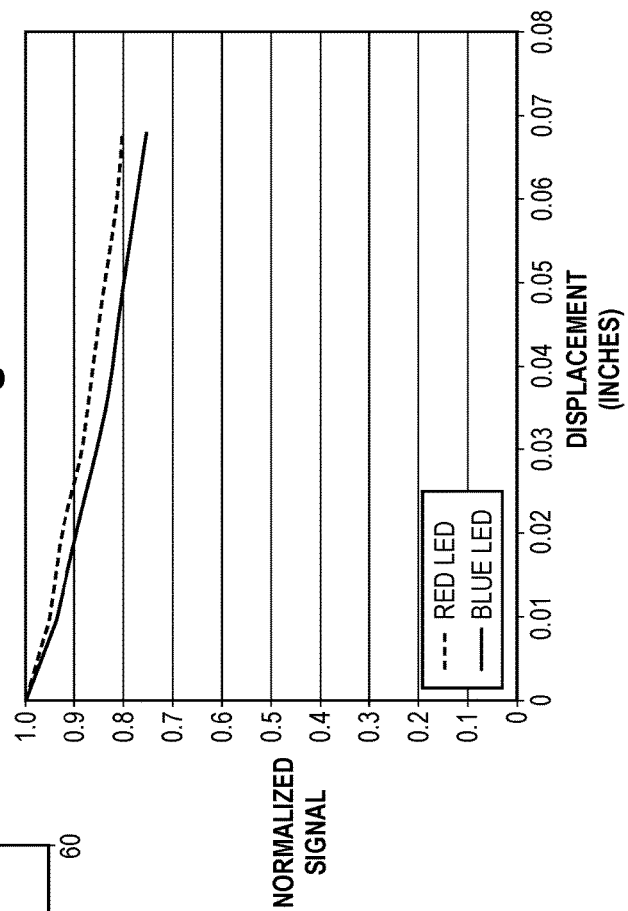
FIG. 11 is a plot of the signal of the photodetector of FIG. 3 as a function of bottle displacement from a home position under illumination by a sensor LED (red line) and a blue spectrum reference LED (blue line).

In the event there is a physical displacement of the bottle in its incubator cell from its nominal or home position, or some other unanticipated change to the optical system occurs, the photodetector signal during illumination from the sensor LED 4 will drop as shown in FIG. 11. Likewise, since the distance between the bottle and the photodetector changes, the photodetector signal during illumination by the blue (reference) LED 10 will drop as well, as also shown in FIG. 11. So instead of a red signal increase and a blue signal decrease, the system will record a decrease in both signals— and the blue change is a larger decrease in signal than normally experienced with bacterial growth (compare the "blue" line in FIG. 11 to the "blue" line in FIG. 10). Therefore, there are two indicators of an abnormal condition. Table 3 shows the conditions that occur from trending the data from the two LEDs. The situation where the photodetector signal from both the blue (reference) and red (sensor) LEDs increases could be caused by a bottle being placed in a cell in the incubator but not pushed to the bottom of the cell to its home position. Later, if the bottle moves further into its holding cell it would reduce the distance between the bottle and the photodetector 5, so both signals would increase.

TABLE 3

Relationship of trended LED signals

|  | Blue LED signal decreases | Blue LED signal increases |
|---|---|---|
| Red LED signal increases | NORMAL condition | Bottle movement |
| Red LED signal decreases | Bottle movement or optical signal changes | Fault condition |

Note: In Table 3, "blue LED signal" means photodetector 5 signal output during illumination of the colorimetric sensor by the blue reference LED 10, FIG. 3; "red LED signal" means photodetector 5 signal output during illumination of the colorimetric sensor by the red sensor LED 4, FIG. 3.

While the above discussion of FIGS. 9-11 pertains to a reference LED with peak wavelength of 465 nm, reference LEDs with other peak wavelengths below about 490 nm are possible. We have also tested 428 nm LEDs for use as a reference LED. The 428 nm LEDs give more change in blue signal as CO2 concentration increases in the bottle as compared to the 465 nm reference LED. While this is not in and of itself too much of a concern, with some bottles other issues may arise which have to be dealt with. Some bottles are constructed as a multi-layer polycarbonate ply with several nylon layers in between the inner and outer layers of polycarbonate. During manufacturing, to provide visual inspection of the nylon layer and confirm that it is a solid layer of nylon up the walls of the bottle, the nylon plastic is impregnated with a fluorophore. If the reference LED is much shorter in wavelength than 428 nm, the fluorophore in the nylon plastic can be activated by the reference LED, causing increased noise to the photodetector signal. In shorter wavelengths, higher energy photons can degrade plastics in the optical system and shorter wavelengths can be an eye hazard to operators of the system if precautions are not taken (such as by wearing suitable protective eyewear when inspecting the optical system during illumination by the reference LED). The degradation of plastic may be ameliorated by selection of UV compatible materials.

In theory, the detector arrangements of this disclosure would work even where the bottle 1 is opaque. The optical system should function with no changes in signal unless the optical system changes. However, with shorter wavelengths for the reference LED (below 400 nm) activation of biological fluorophores present in the sample can occur, causing noise in the detected signal. LEDs are available in emission wavelength down to 240 nm currently; however, the power is low and they are expensive. Reference LED's of around 365 nm may be a practical lower limit using existing electronics for signal gain in the sensing and reference channels since LEDs below this wavelength typically do not have a lot of optical power. In any event, LEDs in the lower (shorter) regions of the spectrum could be made to work using appropriate materials, electronics to handle lower signal values and known methods for elimination of noise in a photodetector signal, e.g., from sources other than the colorimetric sensor such as the bottle, fluorophores present in the bottle material, or autofluorescence in the sample itself.

All questions concerning scope of the invention are to be determined by reference to the appended claims.

I claim:

1. A detection arrangement for blood culture bottle incorporating a colorimetric sensor subject to change of color due to change in pH or $CO_2$ of a sample medium within the blood culture bottle, comprising:
   a sensor LED illuminating the colorimetric sensor;
   a reference LED illuminating the colorimetric sensor;
   a control circuit for selectively and alternately activating the sensor LED and the reference LED; and
   a photodetector, the photodetector measuring reflectance from the colorimetric sensor during the selective and alternating illumination of the colorimetric sensor with the sensor LED and the reference LED, the photodetector generating intensity signals in response to the alternating illumination of the colorimetric sensor with the sensor LED and the reference LED;
   a computer comprising machine executable instructions, wherein the machine executable instructions are configured to:
   receive the intensity signals from the photodetector; and
   determine a displacement of the bottle from a home position based on the intensity signals;
   wherein the reference LED is selected to have a peak wavelength of illumination such that the intensity signals of the photodetector from illumination by the reference LED are not substantially affected by changes in the color of the colorimetric sensor, and
   wherein the peak wavelength of illumination of the reference LED is below about 490 nm.

2. The detection arrangement of claim 1 wherein the reference LED has a peak wavelength of illumination of between about 328 and 470 nm.

3. The detection arrangement of claim 1 wherein the reference LED has a peak wavelength of illumination of between about 450 and 470 nm.

4. The detection arrangement of claim 1, further comprising a computer receiving the intensity signals, the computer including a memory storing a calibration relationship between intensity signals for the reference LED as a function of distance of the bottle from a home position in relation to the detection arrangement.

5. The detection arrangement of claim 4, wherein the memory further stores a calibration relationship between intensity signals for the sensor LED as a function of distance of the bottle from the home position and wherein the computer compensates a drop in intensity signals from the sensor LED due to the bottle being positioned a distance away from the home position in accordance with calibration relationships for the sensor LED and the reference LED.

6. A method for detection of colorimetric sensor incorporated in a blood culture bottle, the colorimetric sensor subject to change of color due to change in pH or $CO_2$ of a sample medium within the blood culture bottle comprising the steps of:
   alternately and repeatedly illuminating the colorimetric sensor with a sensor LED and a reference LED;
   measuring reflectance from the colorimetric sensor due to the illumination of the colorimetric sensor by the sensor LED and reference LED with a photodetector, the photodetector generating intensity signals in response to the alternating illumination of the colorimetric sensor with the sensor LED and the reference LED;
   receiving the intensity signals from the photodetector; and
   determining a displacement of the bottle from a home position based on the intensity signals;
   wherein the reference LED is selected to have a peak wavelength of illumination such that the intensity signals of the photodetector from illumination by the reference LED are not substantially affected by changes in the color of the colorimetric sensor and wherein the peak wavelength of illumination of the reference LED is below about 490 nm.

7. The method of claim 6, wherein the reference LED has a peak wavelength of illumination of between about 328 and 470 nm.

8. The method of claim 6, wherein the reference LED has a peak wavelength of illumination of between about 450 and 470 nm.

9. The method of claim 6, further comprising the step of storing in computer memory a calibration relationship between intensity signals for the reference LED as a function of distance of the bottle from a home position in relation to the sensor LED, reference LED and photodetector.

10. The method of claim 6, further comprising the step of storing in computer memory a calibration relationship between intensity signals for the sensor LED as a function of distance of the bottle from a home position in relation to the sensor LED, reference LED and photodetector.

11. The method of claim 10, further comprising the step of compensating for a drop in intensity signals from the sensor LED due to the bottle being positioned a distance away from the home position in accordance with calibration relationships for the sensor LED and the reference LED.

12. The method of claim 11, wherein the step of compensating comprises the step of determining a displacement value for the bottle using the calibration relationship for the reference LED and using the calibration relationship for the sensor LED to adjust the intensity signal from the photodetector to correct for the displacement of the bottle by the displacement value.

* * * * *